US011344573B2

(12) United States Patent
Abst et al.

(10) Patent No.: US 11,344,573 B2
(45) Date of Patent: May 31, 2022

(54) TREATMENT OF GYNOID LIPODYSTROPHY

(71) Applicant: Merz Pharma GmbH & Co. KGaA, Frankfurt am Main (DE)

(72) Inventors: Harry Frank Abst, Oberursel (DE); Rainer Pooth, Bad Soden/Taunus (DE); Martina Kerscher, Munich (DE); Thomas Hengl, Frankfurt am Main (DE); Birgit Blessmann-Gurk, Mainz (DE); Sabine Otto, Niederdorffelden (DE)

(73) Assignee: MERZ PHARMA GMBH & CO. KGAA, Frankfurt am Main (DE)

( * ) Notice: Subject to any disclaimer, the term of this patent is extended or adjusted under 35 U.S.C. 154(b) by 0 days.

(21) Appl. No.: 16/344,086

(22) PCT Filed: Oct. 24, 2017

(86) PCT No.: PCT/EP2017/077052
§ 371 (c)(1),
(2) Date: Apr. 23, 2019

(87) PCT Pub. No.: WO2018/077825
PCT Pub. Date: May 3, 2018

(65) Prior Publication Data
US 2019/0240253 A1    Aug. 8, 2019

(30) Foreign Application Priority Data
Oct. 28, 2016 (EP) .................................... 16002313

(51) Int. Cl.
| | | |
|---|---|---|
| *A61K 33/06* | (2006.01) | |
| *A61K 9/00* | (2006.01) | |
| *A61K 31/765* | (2006.01) | |
| *A61P 17/00* | (2006.01) | |
| *A61K 31/167* | (2006.01) | |
| *A61K 9/06* | (2006.01) | |
| *A61K 45/06* | (2006.01) | |

(52) U.S. Cl.
CPC ............ *A61K 33/06* (2013.01); *A61K 9/0019* (2013.01); *A61K 9/06* (2013.01); *A61K 31/167* (2013.01); *A61K 31/765* (2013.01); *A61K 45/06* (2013.01); *A61P 17/00* (2018.01)

(58) Field of Classification Search
None
See application file for complete search history.

(56) References Cited

U.S. PATENT DOCUMENTS

| | | | | |
|---|---|---|---|---|
| 6,572,873 | B1 * | 6/2003 | Osman .................... | B65D 83/20 424/423 |
| 2005/0277577 | A1 * | 12/2005 | Hunter .................... | A61B 17/11 424/85.1 |
| 2016/0310444 | A1 * | 10/2016 | Dobak, III ............. | A61K 31/08 |
| 2017/0035678 | A1 * | 2/2017 | Otto ........................ | A61K 8/965 |

FOREIGN PATENT DOCUMENTS

WO    2016005785 A1    1/2016

OTHER PUBLICATIONS

Cuevas, S., et al., Radiesse for Aesthetic Soft Tissue Augmentation, The American Journal of Cosmetic Surgery, First Published Dec. 1, 2006, https://doi.org/10.1177/074880680602300405.*
Graivier, M., et al., Calcium Hydroxylapatite (Radiesse) for Correction of the Mid- and Lower Face: Consensus Recommendations, Plastic and Reconstructive Surgery. 120(6S):55S-66S, Nov. 2007.*
Graivier, M., et al., Calcium Hydroxylapatite (Radiesse) for Correction of the Mid- and Lower Face: Consensus Recommendations, Plastic and Reconstructive Surgery. 120(6S):55S-66S, Nov. 2007 (full version attached) (Year: 2007).*
International Search Report for PCT/EP2017/077052, dated Nov. 17, 2017.
Hexsel et al. "Botanical Extracts Used In The Treatment of Cellulite", American Society for Dermatologic Surgery, vol. 31, Jul. 1, 2005, pp. 866-873.
Hexsel et al. "Cosmeceuticals For Cellulite", Seminars in Cutaneous Medicine and Surgery, vol. 30, No. 3, Jul. 12, 2011, pp. 167-170.
Hexsel, D; Dalforno, T; Hexsel, C; Schilling-Souza, J; Naspolini Bastos, F; Siega, C: "Magnetic Resonance Imaging Of Cellulite Depressed Lesion Successfully Treated by Subcision", Dermatologic Surgery, vol. 42, No. 5, May 2016, pp. 693-696.
F Nuernberger et al. "So-Called Cellulite: An Invented Disease", Journal of Dermatologic Surgery and Oncology, vol. 4, No. 3, Mar. 1, 1978, pp. 221-229.
Alessandra Codinha: "Can Cellulite be Erased?", Harper's Bazaar, May 9, 2014, pp. 1-10.
Hexsel et al. "A Validated Photonumeric Cellulite Severity Scale", European Academy of Dermatology and Venereology, vol. 23, No. 5, May 1, 2009, pp. 523-528.

(Continued)

*Primary Examiner* — H. Sarah Park
(74) *Attorney, Agent, or Firm* — McBee Moore & Vanik IP, LLC

(57) ABSTRACT

The present invention generally relates to the treatment of gynoid lipodystrophy, and more specifically to the use of calcium (hydroxy)phosphate particles in combination with at least one compound capable of reducing local subcutaneous fat in the treatment of gynoid lipodystrophy.

17 Claims, No Drawings

(56) References Cited

OTHER PUBLICATIONS

Goldman et al. "Cellulite: Pathophysiology And Treatment" 2010, p. 15.
Tosti et al. "Update In Cosmetic Dermatology" Second Edition, 2013, p. 53.
Antonella Tosti, et al., "Update In Cosmetic Dermatology," Second Edition, (2013), pp. 52-54.
Doris Hexsel and Mariana Soirefmann, "Cosmeceuticals for cellulite," Seminars in Cutaneous Medicine and Surgery, (2011), vol. 30. No. 3:167-170.
Alessandra Codinha, "Can Cellulite be Erased?", Harper's Bazaar, (2014), pp. 1-10.

* cited by examiner

TREATMENT OF GYNOID LIPODYSTROPHY

CROSS-REFERENCE TO RELATED APPLICATIONS

This application is the National Stage entry of International Application No. PCT/EP2017/077052, filed 24 Oct. 2017, which claims priority to European Patent Application No. 16002313.1, filed 28 Oct. 2016.

BACKGROUND

Field

FIELD OF THE INVENTION

The present invention generally relates to the treatment of gynoid lipodystrophy, and more specifically to the use of calcium (hydroxy)phosphate particles in combination with at least one compound capable of reducing local subcutaneous fat in the treatment of gynoid lipodystrophy.

Description of Related Art

Gynoid lipodystrophy (also known as "cellulite") is a topographic alteration of the skin and subcutaneous adipose tissue. It manifests as a mattress-like or orange peel appearance of the skin, mainly in the buttocks, thighs and abdominal areas. Cellulite mainly affects women because of their weak connective tissue and special skin extracellular matrix structure, among other factors. It is almost ubiquitous in post-pubertal women, affecting 85-98% of all females of age above 20 years. While not a pathologic condition, cellulite represents a serious problem for the affected females, and one of their main aesthetic concerns.

The causes of cellulite are still not exactly clear, even if some of the co-existing factors that trigger, perpetuate or exacerbate cellulite have been identified. These factors include, among others, changes in metabolism of adipose tissue, gender specific dimorphic skin architecture, alteration of connective tissue structure, (i.e. altered fibrous tissue bands), sex-specific expansion of subcutaneous fat, skin laxity, as well as hormonal and genetic factors.

Among these factors, changes in adipose tissue metabolism as well as changes in the dermal architecture are thought to be major factors for the formation of cellulite. Metabolic alterations result in an imbalance between fat production (lipogenesis) and fat breakdown (lipolysis) within adipocytes. This leads to the formation of large adipocytes containing an increased amount of triglycerides which are typical of cellulite, giving the skin the dimpled appearance.

The changes in skin structure associated with cellulite develop in the subcutaneous layer of the skin (subcutis), which is located below the dermis and the epidermis. The fat cells of the subcutaneous fat layer below the dermis layer are arranged in chambers surrounded by bands of fibrous connective tissue called "septa". In male or "normal" adipose tissue, the fibrous septa are arranged in an overlapping criss-cross pattern, creating greater strength of the tissue. In cellulitic tissue of females, on the other hand, the fibrous septa are arranged in parallel to each other, and perpendicular to the skin surface. This structure is weaker and allows for the focal herniation of adipose tissue.

Herniation of adipose tissue means that fat cells that are encased within the perimeters defined by the septa expand with weight gain or water gain, thereby stretching the connective tissue. The connective tissue contracts and hardens holding the skin at a non-flexible length, while the chambers between the septa continue to expand. This results in the displacement of subcutaneous fat (herniation) and areas of the skin being pulled down while adjacent sections bulge outward, resulting in skin dimpling and the "orange peel" appearance.

Many possible treatments of cellulite are nowadays available, including invasive/surgical methods, minimal-invasive methods and non-invasive, topical methods. The invasive/surgical methods mainly address the "fat cell aspect" of cellulite, except the subcision treatment which breaks down/cuts the fibrous septa and thus targets the "connective tissue aspect".

The minimal-invasive methods include, for example, injection lipolysis that also addresses the "fat cell aspect" of cellulite. However, injection lipolysis is difficult to fine tune and does not always give the desired long-term results. Injection lipolysis are also frequently combined with mesotherapy approaches employing multiple injections of different compounds in the (epi)dermis which, however, often do not give the desired treatment result.

As regards the topical methods, a variety of topical products, mainly cosmetic products, are today available on the market. Although these products may be intended to target the connective tissue, it is unlikely that they in fact exert a desired effect on the subcutaneous fat cell layer. Moreover, they typically address only one of the two major aspects of cellulite, i.e. either the "fat cell aspect" or the "connective tissue aspect".

However, despite all the above-mentioned efforts in the treatment of cellulite (gynoid lipodystrophy), the treatment results are often modest at best. Furthermore, the results are often short-lived and ongoing treatment sessions are needed to maintain the results.

OBJECT OF THE INVENTION

It is therefore an object of the present invention to provide an improved treatment of gynoid lipodystrophy, in particular a treatment that is effective, results in the desired aesthetic effects over a longer period, and is well tolerated.

SUMMARY OF THE INVENTION

According to the present invention, the above object is achieved by administering calcium (hydroxy)phosphate particles (e.g., hydroxyapatite) and a compound that is capable of reducing local subcutaneous fat to a subject having gynoid lipodystrophy (cellulite).

This combination treatment approach addresses both the "connective tissue aspect" and the "fat cell aspect" and was found to provide improved treatment results while being well tolerated. Specifically, the combination treatment was found to reduce the unwanted appearance of cellulite, increase the patient satisfaction, and improve the patient's quality of life.

In a first aspect, the present invention relates to the use of calcium (hydroxy)phosphate (e.g., hydroxyapatite) particles in combination with at least one compound capable of reducing local subcutaneous fat in the treatment of gynoid lipodystrophy.

The calcium (hydroxy)phosphate particles for strengthening the connective tissue and said at least one compound for reducing subcutaneous fat may be sequentially or separately administered in the form of injectable compositions by local injection into the lower dermis/upper subcutis and the subcutis, respectively. Preferably, the calcium (hydroxy) phosphate particles are administered in the form of a hydrogel composition, and the at least one fat reducing compound is particularly preferably administered as an injectable composition of polidocanol.

In a second aspect, the present invention provides a method for treating gynoid lipodystrophy comprising administering to a subject in need thereof an effective amount of calcium (hydroxy)phosphate (e.g., hydroxyapatite) particles and an effective amount of at least one compound capable of reducing local subcutaneous fat, wherein the calcium (hydroxy)phosphate particles are administered sequentially or separately with the at least one compound capable of reducing local subcutaneous fat.

In a third aspect, the present invention provides a kit which is suitable for treating gynoid lipodystrophy and comprises a composition of calcium (hydroxy)phosphate (e.g., hydroxyapatite) particles as defined herein and a composition of the at least one compound capable of reducing local subcutaneous fat as defined herein, and optionally instructions for use.

DETAILED DESCRIPTION OF A PREFERRED EMBODIMENT

It was surprisingly found that the use of calcium (hydroxy)phosphate (e.g., hydroxyapatite) particles in combination with a compound capable of reducing local subcutaneous fat (sometimes also referred to herein as "fat reducing compound") provides an improved treatment of gynoid lipodystrophy. More specifically, the combination treatment approach was found to significantly reduce the unwanted appearance of cellulite, to be well tolerated and to lead to an increased patient satisfaction and improvement of the patients quality of life. Furthermore, the combination approach offers the benefit of a flexible and efficient treatment that can be specifically tailored to the patients individual needs.

The calcium (hydroxy)phosphate (e.g., hydroxyapatite) particles are used to address the "connective tissue aspect" by strengthening the skin structure, especially the skin connective tissue. Unexpectedly, injection of small amounts of calcium (hydroxy)phosphate (e.g., hydroxyapatite) particles was found to significantly improve the skin firmness, laxity and flaccidity. Without being bound by theory, it is believed that the injected calcium (hydroxy)phosphate (e.g., hydroxyapatite) particles increases the in situ synthesis of extracellular matrix in general, and stimulates collagen synthesis in particular, thereby increasing the firmness or "strength" of the skin and providing beneficial long-lasting treatment effects.

The compound capable of reducing local subcutaneous fat addresses the "fat cell aspect" of cellulite and adds benefit to the use of calcium (hydroxy)phosphate (e.g., hydroxyapatite) particles. Specifically, the compound is believed to support and complement the action of the calcium (hydroxy) phosphate (e.g., hydroxyapatite) particles by removing subcutaneous local fat, thereby leading to noticeable results that are relatively quickly visible. Furthermore, the fat reducing compound is believed to add to, enhance, or synergistically improve the effects brought about by the calcium (hydroxy) phosphate (e.g., hydroxyapatite) particles.

As used herein, the term "connective tissue aspect" refers to the architectural alterations in the women's subcutaneous connective tissue in connection with cellulite, i.e. the weakening of the skin's specialized connective tissue forming a network of compartments, and the upward pushing of the fat cells into the dermis leading to skin dimpling and nodular characteristics accounting for the clinical appearance of cellulite.

The term "fat cell aspect", as used herein, refers to a metabolic shift of adipocytes in favor of lipogenesis as well as to alterations of adipocytes associated with cellulite, such as an increased adipocyte size and an increased content of triglycerides (triacylglycerides), as well as to the cellular aspect concerning the number of fat cells. The term "addressing", as used herein with respect to the different aspects of gynoid lipodystrophy, refers to the utility of a compound in treating or at least improving the different conditions causing and/or being associated with cellulite.

In the following, the present invention is described in detail referring to "hydroxyapatite" or "hydroxyapatite particles" as an exemplary, particularly preferred "calcium (hydroxy)phosphate" or exemplary, particularly preferred "calcium (hydroxy) phosphate particles". In other words, for the purpose of the following detailed description of the invention, the term "hydroxyapatite" and the term "hydroxyapatite particles" include, are interchangeably used with, or can be replaced with the term "calcium (hydroxy)phosphate" and the term "calcium (hydroxy)phosphate particles", respectively.

The term "calcium (hydroxy)phosphate", as used in the context of the present invention, includes (1) calcium phosphates, such as monocalcium phosphate (MCP) (e.g. $Ca(H_2PO_4)_2$), dicalcium phosphate (DCP) (e.g. $CaHPO_4$), calcium dihydrogen phosphate (CDP) (e.g. $Ca(H_2PO_4)_2$), tricalcium phosphate (TCP) (e.g. $Ca_3(PO_4)_2$) including its α-, α'- and βpolymorphs, octacalcium phosphate (OCP) (e.g. $Ca_8H_2(PO_4).6.5H_2O$), biphasic tricalcium phosphate (BCP; a mixture of two phases: hydroxyapatite (HA) and β-tricalcium phosphate (β-TCP)), and (2) calcium hydroxyphosphates, such as hydroxyapatite. The particles made of calcium (hydroxy)phosphate may be porous and generally have a defined particle size, e.g. a mean particle diameter of about 10 μm to about 100 μm, preferably about 20 μm to about 70 μm. A preferred calcium phosphate is tricalcium phosphate (TCP), in particular β-TCP. A preferred calcium hydroxyphosphate is calcium hydroxyapatite (CaHAP) ($Ca_5(PO_4)_3(OH)$, usually written as $Ca_{10}(PO_4)_6(OH)_2$).

In a first aspect, the present invention relates to the use of hydroxyapatite particles in combination with at least one compound capable of reducing local subcutaneous fat in the treatment of gynoid lipodystrophy.

As used herein, the term "gynoid lipodystrophy" is interchangeably used with the term "cellulite". Gynoid lipodystrophy (or cellulite) generally refers to a condition that gives the skin an uneven, dimpled, orange peel-like appearance. In a more specific sense, "gynoid lipodystrophy" means the herniation of subcutaneous fat within fibrous connective tissue, in particular in the subdermal layer (subcutis) of the skin, which usually manifests topographically as skin dimpling and nodularity, often on the pelvic region (specifically the buttocks), lower limbs, and abdomen. For further explanations and definitions of gynoid lipodystrophy (or cellulite) it may referred to, e.g., Hexsel et al. (J. Eur. Acad. Dermatol. Venereol. 2009, 23: 523-528) and Nürnberger, F. and Müller, G. (J. Dermatol. Surg. Oncol. 1978, 4: 221-229).

The term "treatment", as used herein, is intended to refer to any treatment carried out for cosmetic purposes. The term "cosmetic", as used herein, may be interchangeably used with "aesthetic". Furthermore, the term "subcutaneous fat", as used herein with respect to reducing local subcutaneous fat, is to be broadly construed and particularly relates to fat, fat tissue or fat layer, or a fat deposit in the subcutis or subcutaneous layer (subdermal layer) of skin. The term "fat" within the meaning of the present invention broadly relates to fat and fat constituents, especially triglycerides (triacylglycerides), as well as fat cells (adipocytes).

The term "reducing", as used herein with respect to the compound capable of reducing local subcutaneous fat, broadly means removing, decreasing, diminishing or minimizing local subcutaneous fat. Thus, the term "reducing" is intended to refer to removing, or decreasing (or diminishing or minimizing) the size, volume or amount of fat, a fat deposit, fat cells, a fat layer, a subcutaneous fat layer, a subdermal fat layer, and the like. It should further be appreciated that the term "reducing" does not imply any restrictions regarding the mechanism of fat reduction. Therefore, it includes, for example, decreasing the size or content of fat cells and/or decreasing the number of fat cells.

Reducing in size may be a decrease of the volume of the local subcutaneous fat by at least 5%, at least 10%, at least 25%, at least 30%, at least 40%, at least 50%, at least 60%, at least 70%, at least 80%, at least 90%, or at least 95% in volume, particularly a decrease of the volume of the local subcutaneous fat in the range of 25% to 70%, more particularly in the range of 30% to 65% or 35% to 60%, and most particularly in the range of 40% to 55%.

In accordance with the present invention, the hydroxyapatite particles may be administered, concurrently, sequentially or separately with the at least one compound capable of reducing local subcutaneous fat, preferably sequentially or separately.

The term "concurrently", as used herein, means that administration of hydroxyapatite particles and administration of the at least one compound capable of reducing local subcutaneous fat are overlapping, and in particular means simultaneously or at the same time.

The term "sequentially", as used herein, means that the hydroxyapatite particles and the at least one compound capable of reducing local subcutaneous fat are administered in sequence, for example at an interval or intervals of minutes, hours, days, weeks or months. This is, after administration of one compound (the hydroxyapatite particles or the fat reducing compound), the other compound (the fat reducing compound or the hydroxyapatite particles) can be administered substantially immediately after said one compound, or the other compound can be administered after a time period (e.g., minutes, hours, days, weeks or months) after said one compound. If appropriate, the hydroxyapatite particles and the at least one fat reducing compound may be administered in a regular repeating cycle or in any other suitable administration mode, including multiple (repeated) administration in any order.

The term "separately", as used herein, means that the hydroxyapatite particles and the at least one compound capable of reducing local subcutaneous fat are administered at an interval of, for example, minutes, hours, or a day to several weeks or months. The hydroxyapatite particles and the at least one fat reducing compound may be administered in any order.

Furthermore, the hydroxyapatite particles may be administered before or after, preferably after, the at least one compound capable of reducing local subcutaneous fat. Accordingly, the at least one compound capable of reducing local subcutaneous fat may be administered before or after, preferably before, the hydroxyapatite particles.

It is further contemplated within the present invention that one or both of the hydroxyapatite particles and the at least one compound capable of reducing local subcutaneous fat is/are repeatedly administered. This is, administration by local injection of hydroxyapatite particles may be carried out more than once, for example two, three, four or more times, either before or after administration by local injection of the at least one compound capable of reducing local subcutaneous fat once or two, three, four or more times. In particular, the hydroxyapatite particles may be administered by local injection only once or two or three times, preferably once, after administration by local injection of the at least one compound capable of reducing local subcutaneous fat once, two time or three times, preferably one or two times.

The interval between any two consecutive administrations of hydroxyapatite particles and/or the at least one fat reducing compound may be as short as technically possible, i.e. within one or several minutes, but is preferably daily, every second day, every three days, weekly, biweekly, monthly, twice a year, yearly, or less often. Preferably, between any two successive injections, there may be a time interval of about 1 week to about 8 weeks or of about 1 week to about 4 weeks. Exemplarily, the time interval may be in the range of from 5 to 9 days, 9 to 16 days, 16 to 23 days, or 23 to 30 days. Clinically viable administration schemes may be readily determined by the person skilled in the art.

Within the framework of the present invention, each "administration" or "administration by (local) injection" is intended to mean application within one treatment session. It is further contemplated that an "administration" or "injection" may include a single injection as well as multiple injections (or multiple "punctures") within one treatment session. Hence, multiple injections (punctures) of hydroxyapatite particles and/or of the at least one fat reducing compound within a single session is also encompassed by the present invention. Each puncture is a penetration of the mammal's skin with an injection tool, such as a needle accompanied by applying the hydroxyapatite particles or the at least one fat reducing compound through said injection tool to the target site. Exemplarily, the skin may be punctured once, twice, 10 times, 50 times, 100 times or more times.

The hydroxyapatite particles and the at least one compound capable of reducing local subcutaneous fat are generally administered by local cutaneous injection, i.e. by injection into the skin. Preferably, the hydroxyapatite particles are administered by injection into the dermis, the subcutis, or both the dermis and subcutis, and more preferably into the deep dermis, upper subcutis, or the deep dermis and upper subcutis.

The term "deep" dermis generally refers to the reticular region of the dermis, i.e. the region lying deep in the papillary region and being usually much thicker than the papillary region, which is located between the epidermis and the reticular region. The reticular region of the dermis is composed of dense irregular connective tissue, and has its name from the dense concentration of collagenous, elastic, and reticular fibers.

The at least one compound capable of reducing local subcutaneous fat is preferably administered by injection into the subcutis, especially into the subcutaneous (subdermal) fat layer or fat deposit.

If the dermis and/or subcutis, preferably the deep dermis and/or upper subcutis, are punctured more than once in a single treatment session for administration of a given amount of hydroxyapatite particles, the distance between two punctures (spacing of the punctures) is preferably at least 0.25 cm, more preferably 0.25 cm to 3.0 cm, 0.25 cm to 2.5 cm or 0.5 cm to 2.0 cm, and most preferably 0.75 cm to 1.25 cm or about 1 cm. In other words, there are preferably not more than 4 punctures per square centimeter (cm²), more preferably not more than 2 punctures per cm², even more preferably not more than 1 punctures per cm² or even less such as not more than 0.5 or not more than 0.25 or not more than 0.1 punctures per cm².

If the subcutis (or subcutaneous fat layer or fat deposit) is punctured more than once in a single treatment session for administration of a given amount of the at least one compound capable of reducing local subcutaneous fat, the distance between two punctures (spacing of the punctures) is preferably at least 0.25 cm, more preferably 0.25 cm to 3.0 cm or 0.5 cm to 2.0 cm, and most preferably 0.75 cm to 1.5 cm or about 1 cm. In other words, there are preferably not more than 4 punctures per square centimeter (cm²), more preferably not more than 2 punctures per cm², even more preferably not more than 1 punctures per cm² or even less such as not more than 0.5 or not more than 0.25 or not more than 0.1 punctures per cm².

Furthermore, if the hydroxyapatite particles and the at least one fat reducing compound are administered in the form of injectable compositions, the volume of the liquid or semi-solid (i.e., viscous) composition injected into a subject per injection may be in the range of several microliters to several milliliters. The amount injected per injection site (puncture) may be in the range of 5 µl to 1000 µl, particularly in the range of 10 µl to 300 µl. The hydroxyapatite particles are preferably injected in an amount of 10 µl to 75 µl, more preferably 15 µl to 50 µl or 20 µl to 30 µl, per injection site. The at least one fat reducing compound is preferably administered in an amount of 30 µl to 300 µl, more preferably 50 µl to 200 µl or 75 µl to 150 µl, per injection site. A person skill in the art is readily able to determine appropriate amounts or volumes for the individual case.

In accordance with the present invention, the subject to be treated may be overweight. As used herein, a "subject" is any individual which has cellulite, i.e. any individual in need of a cellulite treatment. Further, the term "overweight", as used herein, refers to a body mass index (BMI), defined as the body mass in kg divided by the square of the body height, of at least 25 kg/m², at least 30 kg/m² or at least 35 kg/m². Furthermore, the subject may be a subject afflicted with severe cellulite. Within the meaning of the present invention, "severe cellulite" preferably corresponds to a total sum of scores of items (a) and (b) of the Hexsel, Dal'Forno, and Hexsel Cellulite Severity Scale (CSS) (Hexsel et al., A validated photonumeric cellulite severity scale, J. Eur. Acad. Dermatol. Venereol. 2009, 23: 523-528) of 4, 5 or 6, wherein item (a) denotes the number of evident depressions and item (b) denotes the depth of depressions, and both items (a) and (b) are graded from 0 to 3.

Suitable hydroxyapatite particles for use herein are any particles of a given size made of hydroxyapatite. "Hydroxyapatite" refers to a mineral species of the phosphate family with the formula $Ca_5(PO_4)_3(OH)$, usually written as $Ca_{10}(PO_4)_6(OH)_2$ to stress the fact that the lattice of the crystalline structure contains two molecules. Hydroxyapatite belongs to the crystallographic apatite family, which are isomorphic compounds having the same hexagonal structure. This compound has been used as a biomaterial for many years in various medical specialties. Preferably, the hydroxyapatite particles have an atomic ratio of calcium to phosphorus of 1.67±0.03.

Preferably, the hydroxyapatite particles used within the present invention are spherical or essentially spherical particles. Furthermore, the hydroxyapatite particles preferably have a D-ratio of greater or equal to 0.9. The D-ratio is defined as the ratio of the calculated diameter of a perfect circle based on the cross sectional area of the particle to the maximum diameter measured through that cross sectional centroid.

Furthermore, the mean size of the hydroxyapatite particles in diameter is usually less than 200 µm, preferably in the range of about 10 µm to 100 µm, more preferably in the range of about 20 µm to about 70 µm, and most preferably in the range of about 25 µm to about 45 µm in diameter. In addition, the hydroxyapatite particles may not comprise more than 10 wt. % of particles having a diameter of 20 µm or less, or more than 5 wt. % of particles having a diameter of 25 µm or less, and/or more than 5 wt. % of particles having a diameter of 45 µm or greater, or more than 2 wt. % of particles having a diameter of 70 µm or greater. Moreover, the hydroxyapatite particles may have a BET surface area of equal to or less than 0.10 m²/g.

In accordance with the present invention, the hydroxyapatite particles are preferably administered as an injectable composition, in particular as an injectable composition in the form of a hydrogel (hydrogel composition). The injectable composition generally comprising the hydroxyapatite particles and a pharmaceutically acceptable carrier such as an aqueous solution, an organic solvent, a mixture of an aqueous solution and an organic solvent, or a gel. The pharmaceutically acceptable carrier generally serves as solvent or suspending agent for the hydroxyapatite particles. Preferably, the pharmaceutically acceptable carrier is a gel, e.g. a hydrogel. The term "pharmaceutically acceptable", as used herein, refers to materials or substances that are suitable for use in contact with the tissues of humans and mammals without undue toxicity, irritation, allergic response, and the like.

The term "gel" or "hydrogel", as used herein, generally refers to a water-swollen three-dimensional network consisting of crosslinked or non-crosslinked polymer chains. Within the present invention, the gel is preferably a cohesive gel, i.e. a gel having the capacity not to dissociate, because of the affinity of its polymer chains for each other. Cohesivity is important for the solid and fluid phases of a gel to remain intact, and thus for forming a stable gel.

Preferably, the injectable composition of hydroxyapatite particles is in the form of a hydrogel comprising the hydroxyapatite particles and at least one polysaccharide. The polysaccharide gel provides a (carrier) matrix for suspending or dispersing the hydroxyapatite particles. The "polysaccharide" is not particularly limited and may include, for example, cellulose, cellulose ester and cellulose ether derivatives such as cellulose acetate (CA), carboxymethyl cellulose (CMC), carboxyethyl cellulose (CEC), carboxypropyl cellulose (CPC), carboxymethyl ethylcellulose (CMEC), methyl cellulose (MC), ethyl cellulose (EC), hydroxyethyl cellulose (HEC), hydroxyethyl methylcellulose (HEMC) and hydroxypropyl methylcellulose (HPMC), hyaluronic acid (HA), dextran, carboxymethyldextran, carboxymethylstarch, chondroitin sulfate, dermatane sulfate, keratin, keratin sulfate, chitosan, chitin, pectin, carrageenan, xanthan, heparin, heparin sulfate and alginate. Preferably, the polysaccharide is selected from the group consisting of hyaluronic acid (HA), carboxylated cellulose derivatives (e.g., carboxymethyl cellulose (CMC)), and mixtures thereof.

The polysaccharide(s) of the gel matrix may be (independently from each other) crosslinked and/or non-crosslinked. A "crosslinked gel" or "crosslinked gel matrix" within the context of the present invention preferably refers to a (hydro)gel or (hydro)gel matrix which is covalently crosslinked using a crosslinking agent. Optionally, the injectable composition may contain one or more non-crosslinked polysaccharides which may be the same as or different to the crosslinked polysaccharide(s). The term "crosslinking agent" or "crosslinker", as used herein, refers to a compound having at least two functional groups (i.e. two, three or more epoxide functional groups) capable of reacting with polysaccharide polymers (e.g., hyaluronic acid) to form covalent (intra- and/or intermolecular) crosslinks.

Whilst the term "crosslinking agent" or "crosslinker" is not specifically limited within the present invention, the crosslinker is preferably a diepoxide crosslinker, e.g., 1,4-butanediol diglycidyl ether (BDDE). Other suitable diepoxid crosslinkers include, but are not limited to ethylene glycol diglycidyl ether (EGDGE), 1,6-hexanediol diglycidyl ether, polyethylene glycol diglycidyl ether, polypropylene glycol diglycidyl ether, polytetramethylene glycol digylcidyl ether, neopentyl glycol digylcidyl ether, polyglycerol polyglycidyl ether, 1,2,7,8-diepoxyoctane, 3-(bis(glycidoxymethyl)-methoxy)-1,2-propanediol, 1,4-cyclohexanedimethanol diglycidyl ether, 4-vinyl-1-cyclohexene diepoxide, 1,2,5,6-diepoxycyclooctane, and bisphenol A diglycidyl ether.

Preferably, the injectable composition comprises only one type of polysaccharide or a mixture of two different polysaccharide types (e.g., CMC and/or HA). The term a "type of polysaccharide", as used herein, also includes mixtures of materials of the same polysaccharide but having a different mean molecular weight and/or a mixture of the same polysaccharide in crosslinked and/or non-crosslinked form. Advantageously, the at least one polysaccharide is selected from crosslinked or uncrosslinked carboxymethylcellulose, crosslinked or uncrosslinked hyaluronic acid, or a mixture thereof, in particular (uncrosslinked) carboxymethylcellulose or crosslinked hyaluronic acid, or a mixture thereof. Preferably, the mean molecular weight of the hyaluronic acid is in the range of about $2.5 \times 10^5$ Da and $4 \times 10^6$ Da, more preferably in the range of about $1 \times 10^6$ Da and $3 \times 10^6$ Da. Furthermore, the hyaluronic acid is preferably crosslinked with a diepoxide crosslinker, in particular BDDE.

The hydroxyapatite particles may be present in the injectable composition in an amount of about 5 to 45 vol. %, preferably 10 to 40 vol. %, more preferably 15 to 35 vol. %, and most preferably 20 to 30 vol. %. Furthermore, the at least one polysaccharide may be present in the injectable composition in a total amount of about 0.01% to 5.0% (mass/volume), preferably about 0.1% to 4.0% (mass/volume), more preferably, about 0.5% to 3.0% (mass/volume), and most preferably about 1.0% to 2.5% (mass/volume) or 1.5 to 2.0% (mass/volume).

Within the context of the present invention, the injectable composition of hydroxyapatite particles may further comprise at least one additional pharmaceutically acceptable active ingredient. Said additional pharmaceutically acceptable ingredient may be selected from the group of ingredients promoting collagen biosynthesis. The additional pharmaceutically acceptable active ingredient promoting collagen biosynthesis can be selected from the group consisting of retinol, rhamnose, saponins, petroselinic acid, conjugated linoleic acid, hibamata extract, pentapeptides, hexapeptides and poly-L-lactic acid.

Furthermore, the injectable composition of hydroxyapatite particles may further comprise an anaesthetic and/or anti-inflammatory agent. The anaesthetic is preferably a local anaesthetic, preferably lidocaine, in a concentration of, for example, 0.05 wt. % to 5.0 wt. %, 0.1 wt. % to 4.0 wt. %, 0.2 wt. % to 3.0 wt. %, 0.3 wt. % to 2.0 wt. %, or 0.4 wt. % to 1.0 wt. %.

Moreover, the injectable composition of hydroxyapatite particles may further comprise one or more compounds selected from the group consisting of polyols, vitamins, amino acids, metals, antioxidants, and mineral salts. Suitable polyols for use herein include, but are not limited to, glycerin, mannitol, sorbitol, propylene glycol, erythritol, xylitol, maltitol, and lactitol. Particularly suitable for use herein is mannitol and glycerol. Preferably, the polyol is glycerol, optionally in combination with one or more of the aforementioned polyol compounds, in particular mannitol. The polyol(s) may, for example, be included in the injectable dermal filler composition in a concentration of 0% (no polyol) to 20% (volume/volume), 0.1% to 19% (volume/volume), 1% to 18%, 2% to 17%, or 3% to 13% (volume/volume), in particular in a concentration of 5% to 12% or 7% to 10% (volume/volume).

In a particular embodiment, the injectable composition of hydroxyapatite particles is a sterile, non-pyrogenic injectable composition of spherical hydroxyapatite particles in an aqueous based gel carrier, the composition consisting of 55.7 wt. % calcium hydroxyapatite particles having a diameter of from about 25 µm to about 45 µm, 36.6 wt. % sterile water for injection (USP), 6.4 wt. % glycerin (USP), and 1.3 wt. % sodium carboxymethyl cellulose (USP). Another particularly suitable injectable composition of hydroxyapatite particles for use is the soft tissue filler Radiesse® or diluted versions thereof. Radiesse® comprises calcium hydroxyapatite microspheres, a CMC gel matrix and glycerol.

In accordance with the present invention, the at least one compound capable of reducing local subcutaneous fat may be selected from the group consisting of:

(i) compounds that stimulate the β2-adrenergic pathway directly or block the activity of cellular phosphodiesterases, such as paraxanthine, caffeine, ciclostamide, amirone, tolfentrine, revizinone and enoximone, (ii) adipocytolytic compounds (i.e. compounds destroying directly or indirectly adipocytes), such as polidocanol, cationic-amphiphilic compounds, trifluoperazine, nebivolol, duloxetine, phosphatidylcholine (PC), bile acids including deoxycholate (DC), chenodeoxycholic acid (CDCA), ursodeoxycholate (UDCA) and lithocholic acid (LCA), (iii) proapoptotic compounds, such as resveratol and phytoalexin, (iv) compounds impairing differentiation of pre-adipocytes, such as antagonists of the peroxisome proliferator-activated receptor-gamma such as an antagonist of the peroxisome proliferator-activated receptor-gamma of herbal origin, particularly naringenin, luteolin, phenylacrylic acid (rosmarinic acid), diosmetin and poncirin, (v) pentacyclic triterpenoid compounds, including ursolic acid, betulinic acid, moronic acid, oleanolic acid, maslinic acid, asiatic acid, corosolic acid, alpha boswellic acid, beta boswellic acid, acetyl alpha boswellic acid, acetyl beta boswellic acid, acetyl keto alpha boswellic acid, acetyl keto beta boswellic acid, madecassic acid, arjunolic acid, enoxolone, enoxolone, and carbenoxolone, (vi) other compounds such as fluoxetine, glycyrrhizic acid, maslinic acid, ginsenoide Rh2, betulinic acid, moronic acid, deoxycholic acid, obeticholic acid, erythrodoil, ursolic acid, uvaol, betulinic acid, becarben, carbenoxolone, glabridin, and (vii) combinations of one or more of (i) to (vi).

wherein the at least one compound capable of reducing local subcutaneous fat is preferably polidocanol.

Preferably, the at least one compound capable of reducing local subcutaneous fat is selected from the group consisting of polidocanol, fluoxetine, pentacyclic triterpenoid compounds, obeticholic acid and deoxycholic acid. Particularly preferred for use herein is polidocanol (hydroxypolyethoxydodecan).

The pentacyclic triterpenoid compounds generally exhibit, in addition to the desired adipocytolytic effect, pharmaceutically acceptable supportive activities (e.g. pro-lipolytic activity and apoptosis-inducing capacity) enhancing the desired fat-tissue reducing effect. Further, the suggested compounds can be safely purified from plants, thereby avoiding the use of material from animal sources and eliminating the risk of animal transmitted diseases.

The pentacyclic triterpenoid compounds preferably have the following structure according to formula (I)

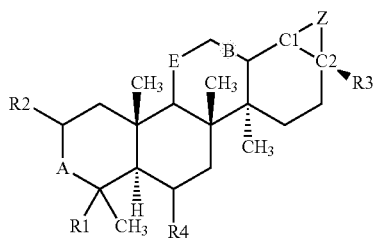

wherein:

R1 is selected from the group consisting of —$CH_3$, —$CH_2OH$, and —$COO^-X^+$, wherein $X^+$ is a proton or a pharmaceutically acceptable cation;

R2 is hydrogen or —OH;

R3 is selected from the group consisting of —$COO^-X^+$, —$CH_3$, and —COORa, wherein $X^+$ is a proton or a pharmaceutically acceptable cation and wherein Ra is a $C_{1-4}$-alkyl residue; in particular R3 is —$COO^-X^+$ R4 is hydrogen or —OH;

C1 and C2 are each a carbon atom wherein the valency of C1 is replenished by hydrogen when the bond to z is a single bond;

z represents a bivalent residue selected from the groups consisting of

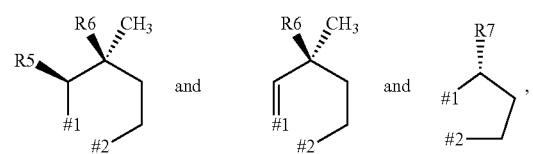

wherein

1 represents the binding site to the carbon atom C1 of the remaining structure according to formula (I),

2 represents the binding site to the carbon atom C2 of the remaining structure according to formula (I), R5 is —$CH_3$ or hydrogen; R6 is —$CH_3$, hydrogen, or —$COO^-X^+$, and R7 is a $C_{2-4}$ alkenyl residue or a $C_{1-4}$ alkyl residue, preferably a $C_{2-4}$ alkenyl residue;

A is a bivalent residue selected from the groups consisting of

—CH(OH)—, —CH(OAc)—, —CO—, and —$CH_2$—, where Ac is an acyl group, in particular an acetyl group (—CO—$CH_3$) or a succinyl group (—CO—$CH_2CH_2$—COOH); and B represents a double or a single bond; E represents —$CH_2$— or —CO—, in particular wherein one of R1, R3 or R6 is —$COO^-X^+$, wherein $X^+$ is a proton or a pharmaceutically acceptable cation.

A "pharmaceutically acceptable salt" within the meaning of the present invention is any salt that exhibits a comparably low toxicity and is acceptable for pharmaceutical purposes. Examples of pharmaceutically acceptable salts may comprise a cation selected from the group consisting of an alkali metal (in particular, $Na^+$ and/or $K^+$), a proton (i.e., $H^+$), an alkaline earth metal (in particular, $Mg^{2+}$ and/or $Ca^{2+}$), ammonium ($NH_4^+$), $Fe^{2+}$, $Fe^{3+}$, $Zn^{2+}$, $Sn^{2+}$, and an organic amine cation, or may comprise an anion selected from the group consisting of a halogen (in particular $Cl^-$, $Br^-$, $I^-$ and/or $F^-$), $OH^-$, $H_2PO_4^-$, $HPO_4^{2-}$, $PO_4^-$, $SO_4^{2-}$, an anion of an organic acid (e.g., acetate, methanoate, propionate, a salt of a fatty acid, gluconate, lactate, citrate, etc.), an organic sulfonate, an organic sulfate, and organic phosphate.

Those skilled in the art will appreciate that the carbon atoms C1 and C2 together with the bivalent residue z form a 5- or 6-membered ring, optionally substituted one, two or three times by —$CH_3$ and substituent(s) R5, R6 and/or R7 as indicated above. Thereby the triterpenoid compound becomes a pentacyclic triterpenoid compound. The core structure (scaffold) of the pentacyclic triterpenoid structure of the present invention may be an ursane (alpha-Amryn), an oleanane (beta-Amryn) or a lupane ring structure.

In the above structure, $X^+$ may be any proton or a pharmaceutically acceptable cation. It is preferably a one-fold positively charged ion. For example, the cation may be selected from the group consisting of an alkali metal (in particular, $Na^+$ and/or $K^+$), an alkaline earth metal (in particular, $Mg^{2+}$ and/or $Ca^{2+}$), ammonium ($NH_4^+$), $Fe^{2+}$, $Fe^{3+}$, $Zn^{2+}$, $Sn^{2+}$, and an organic amine. Preferably, the cation is a proton ($H^+$) or an alkali metal (in particular, $Na^+$ and/or $K^+$).

Preferably, at least one of R1, R3 or R6 is —$COO^-X$, wherein $X^+$ is a proton or a pharmaceutically acceptable cation. R7 is preferably —C(=$CH_2$)—$CH_3$ and/or A is —CH(OH)— or —CO—. More preferably, one of R1, R3 and R6 is —$COO^-X^+$, wherein $X^+$ is a proton or a pharmaceutically acceptable cation. Then, the other residues do preferably not comprise a carboxyl group. Particularly preferred, R1 is —$CH_3$. Furthermore, in the pentacyclic triterpenoid compound according to formula (I), in group z, R7 is preferably —C(=$CH_2$)—$CH_3$. Preferably, in the pentacyclic triterpenoid compound according to formula (I), A is —CH(OH)—, —CH(OAc)— (wherein "Ac" represents an acetyl moiety (—CO—$CH_3$) or a succinyl group (—CO—$CH_2CH_2$—COOH)), or —CO—. Preferably, in the pentacyclic triterpenoid compound according to formula (I), B represents a double or a single bond.

In a preferred embodiment, the triterpenoid compound has the following structure according to formula (II)

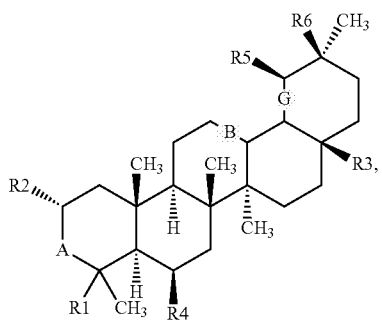

wherein the residues R1 to R6, A and B are as defined above and wherein G is a single or a double bond.

In a preferred embodiment, the triterpenoid compound has the following structure according to formula (III)

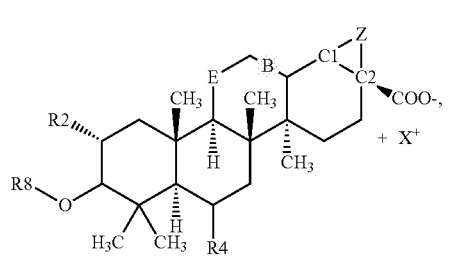

wherein:
C1 and C2 are each a carbon atom;
R2 is hydrogen or —OH;
R4 is hydrogen or —OH, in particular hydrogen;
R5 is —CH$_3$ or hydrogen;
R6 is —CH$_3$, hydrogen, or —COO$^-$X$^+$; and
R8 is hydrogen or —CO—CH$_3$; or
R8 is Ac, where Ac is an an acyl group, in particular an acetyl group (—COCH$_3$) or a succinyl group (—CO—CH$_2$CH$_2$—COOH); and
z represents a bivalent residue selected from the group consisting of

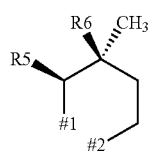 and 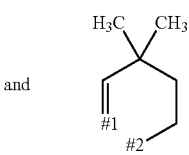 and 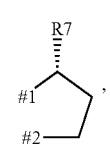, wherein
1 represents the binding site to the carbon atom C1 of the remaining structure according to formula III,
2 represents the binding site to the carbon atom C2 of the remaining structure according to formula III, and
B represents a double or a single bond; and
X$^+$ is a proton or a pharmaceutically acceptable cation.

In a particularly preferred embodiment, the triterpenoid compound has a structure according to any of formulae (IV) to (VII):

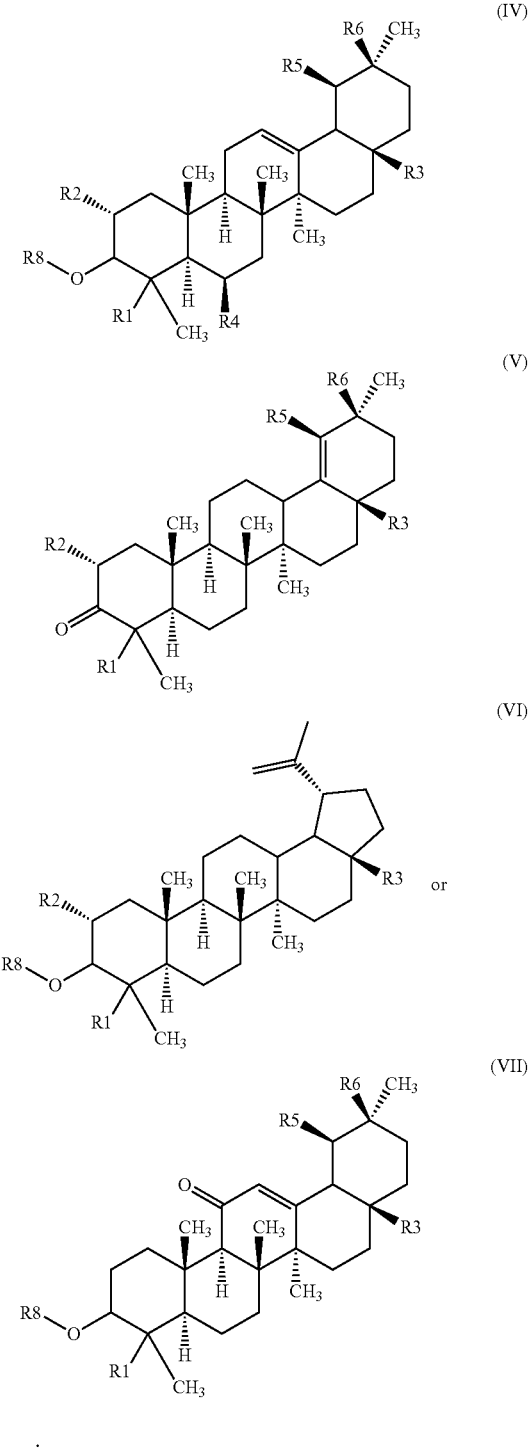

wherein:
R1 is —CH$_3$, —CH$_2$—OH, or —COO$^-$X$^+$, wherein X$^+$ is a proton or a pharmaceutically acceptable cation, in particular wherein R1 is —CH$_3$;
R2 is hydrogen or —OH;
R3 is —COO$^-$X$^+$ or —CH$_3$, wherein X$^+$ is a proton or a pharmaceutically acceptable cation, in particular wherein R6 is —COO$^-$X$^+$;
R4 is hydrogen or —OH;
R5 is —CH$_3$ or hydrogen;
R6 is —CH$_3$, hydrogen, or —COO$^-$X$^+$, and
R8 is hydrogen or —CO—CH$_3$ or —CO—CH$_2$CH$_2$—COOH wherein one of R1, R3 or R6 is —COO⁻X⁺, wherein X⁺ is a proton or a pharmaceutically acceptable cation.

Even more preferably, the triterpenoid compound has a structure according to any of formulae (VII) to (XII):

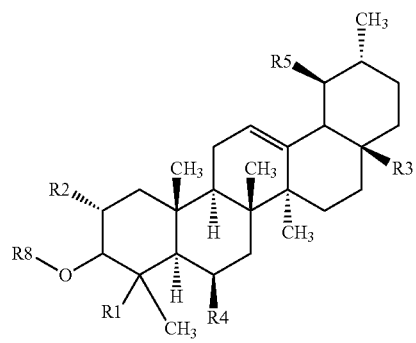

(VII)

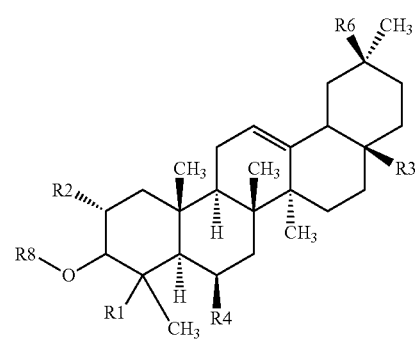

(IX)

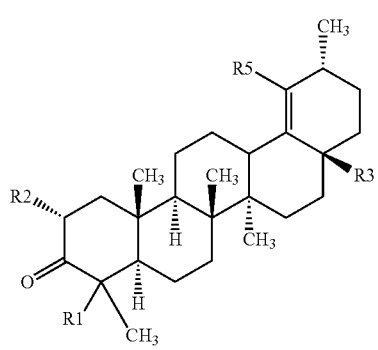

(X)

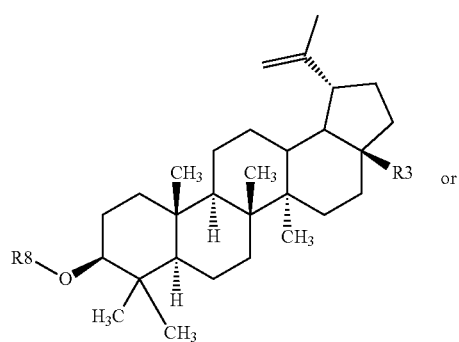

(XI)

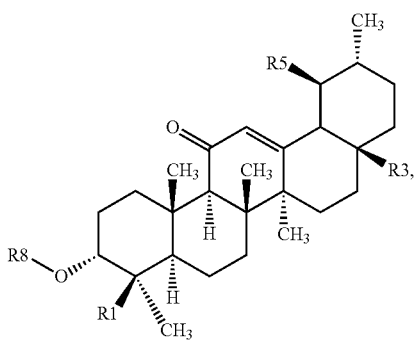

(XII)

wherein the residues R1 to R6 and R7 are as defined as above.

Within the present invention, it is preferred to use pentacyclic triterpenoid compounds which are obtainable from plants. In a preferred embodiment, the triterpenoid compound is selected from the group consisting of: ursolic acid, betulinic acid, moronic acid, oleanolic acid, maslinic acid, asiatic acid, corosolic acid, alpha boswellic acid, beta boswellic acid, acetyl alpha boswellic acid, acetyl beta boswellic acid, acetyl keto alpha boswellic acid, acetyl keto beta boswellic acid, madecassic acid, arjunolic acid, enoxolone, and pharmaceutically acceptable salts thereof. Asiatic acid is particularly preferred for use herein. Also, enoxolone and carbenoxolone are particular suitable compounds.

Ursolic acid is also known as (1S,2R,4aS,6aR,6aS,6bR, 8aR,10S,12aR, 14bS)-10-hydroxy-1,2,6a,6b,9,9,12a-heptamethyl-2,3,4,5,6,6a,7,8,8a,10,11,12,13, 14b-tetra-decahydro-1H-picene-4a-carboxylic acid, prunol, malol, beta-ursolic acid, NSC4060, CCRIS 7123, TOS-BB-0966, and 3-beta-hydroxyurs-12-en-28-oic acid. It is, for example, found in and extractable from the peels of a variety of fruits as well as in herbs and spices like rosemary and thyme.

Betulinic acid is known as (3β)-3-hydroxy-lup-20(29)-en-28-oic acid, 3a-hydroxy-methyl-1-isopropenyl-5α,5β,8, 8,11α-pentamethyl-icosahydrocyclopenta[a]-chryse-nic acid, betulic acid and mairin. It is, for example, found in and extractable from the bark of a variety of plants such as, e.g., from the bark of the white birch *Betula pubescens*.

Moronic acid is also known as (4aS,6aR,6aS,6bR,8aS, 12aS,14aS)-2,2,6a,6b,9,9,12a-heptamethyl-10-oxo-4,5,6, 6a,7,8,8a, 11,12,13,14,14a-dodeca-hydro-3H-picene-4a-carboxylic acid, ambronic acid and 3-oxoolean-18-en-28-oic acid, and oleanolic acid. It is, for example, found in and extractable from *Rhus javanica* and mistletoe *Phoradendron reichenbachianum*.

Oleanolic acid is also known as (4aS,6aR,6aS,6bR,8aR, 10S,12aR,14bS)-10-hydroxy-2,2,6a,6b,9,9,12a-heptamethyl-1,3,4,5,6,6a,7,8,8a,10,11,12,13,14b-tetra-decahydropicene-4a-carboxylic acid and oleanic acid. It is, for example, found in and extractable from, e.g., olive oil, American pokeweed (*Phytolacca americana*), garlic, and *Syzygium* species.

Maslinic acid is also known as (4aS,6aR,6aS,6bR,8aR, 10R,11R,12aR, 14bS)-10,11-dihydroxy-2,2,6a,6b,9,9,12a-heptamethyl-1,3,4,5,6,6a,7,8,8a,10,11,12, 13,14b-tetradecahydropicene-4a-carboxylic acid, 2α-hydroxyoleanolic acid and (2a,3R)-2,3-dihydroxyolean-12-en-28-oic acid. It is, for example, found in and extractable from olive oil. However, the in vivo activity is lower than that of, e.g. asiatic acid or carbenoxolone.

Asiatic acid is known as (1S,2R,4aS,6aR,6aS,6bR,8aR, 9R,R,10R,12aR, 14bS)-10,11-dihydroxy-9-(hydroxymethyl)-1,2,6a,6b,9,12a-hexamethyl-2,3,4,5,6,6a, 7,8, 8a,10, 11,12,13,14b-tetradecahydro-1H-picene-4a-carboxylic acid. It is, for example, found in and extractable from *Centella asiatica* or *Syzygium claviflorum* and is particularly suited for use herein. It can be formulated in a broad range of concentrations, has a high stability over a long period of time (months) and particularly good in-vitro and in-vivo activity. Furthermore, it was found that the compositions comprising asiatic acid do not lead to nerve injury. The compositions are particularly stable over a long period of time and have particularly good in vitro and in vivo activity.

Corosolic acid is also known as (1S,2R,4aS,6aR,6aS,6bR, 8aR,10R, 11R,12aR,14bS)-10,11-Dihydroxy-1,2,6a,6b,9,9, 12a-heptamethyl-2,3,4,5,6,6a,7,8, 8a,10,11,12,13,14b-tetradecahydro-1H-picene-4a-carboxylic acid, glucosol, corsolic acid, colosic acid and 2α-hydroxyursolic acid. It is, for example, found in and extractable from *Lagerstroemia speciosa*.

Enoxolone is also known as 18β-glycyrrhenic acid (the aglycon of glycyrrhizic acid), glycyrrhetic acid or (2S,4aS, 6aS,6bR,8aR,10S,12aS,12bR,14bR)-10-hydroxy-2,4a,6a, 6b,9,9,12a-heptamethyl-13-oxo-1,2,3,4,4a,5,6,6a,6b,7,8,8a, 9,10,11,12,12a,12b,13,14b-icosahydropicene-2-carboxylic acid. The corresponding succinate ester is carbenoxolone (CAS 5697-56-3), which has a high stability over a long period of time and particularly good in vitro and in vivo activity.

Arjunolic acid is also known as 2,3,2,3-Trihydroxyolean-12-en-28-oic acid or (2a,3P,4a)-2,3,23-Trihydroxy-olean-12-en-28-oic acid. It is, for example, found in and extractable from *Terminalia arjuna, Combretum nelsonii* and/or *Leandra chaeton*.

Madecassic acid is also known as Brahmic acid or (1S, 2R,4aS,6aR,6aS, 6bR,8R,8aR,9R,10R,11R,12aR,14bS)-8, 10,11-trihydroxy-9-(hydroxymethyl)-1,2,6a,6b,9,12a-hexamethyl-2,3,4,5,6,6a,7,8,8a, 10,11,12,13,14b-tetradecahydro-1H-picene-4a-carboxylic acid. It is, for example, found in from *Centella asiatica*.

Beta-boswellic acid is also known as (3a,43)-3-Hydroxyurs-12-en-23-oic acid, 3α-Hydroxyurs-12-en-24-oic acid. It is, for example, found in from *Boswellia* species such as, e.g., *Boswellia serrata*. Alpha boswellic acid is also known as (3a,41)-3-Hydroxyolean-12-en-23-oic acid, 3α-Hydroxyolean-12-en-24-oic acid. It is, for example, found in and extractable from *Boswellia* species such as, e.g., *Boswellia serrata*. Likewise, also acetyl beta-boswellic acid, acetyl keto beta-boswellic acid, and acetyl alpha-boswellic acid are each exemplarily found and extractable from *Boswellia* species such as, e.g., *Boswellia serrata*. Further, the respective non-acetylated precursors may also be acetylated synthetically by means of standard methods.

Particularly suitable pentacyclic triterpenoid compounds include compounds having an ursane core structure (alpha-Amryn) selected from the group consisting of ursolic acid, beta boswellic acid, corosolic acid, asiatic acid, madecassic acid, acetyl beta boswellic acid, acetyl keto beta boswellic acid, and pharmaceutically acceptable salts thereof. Further particularly suitable pentacyclic triterpenoid compounds include compounds having an oleanane core structure (beta-Amryn) selected from the group consisting of maslinic acid, oleanolic acid, moronic acid, arjunolic acid, alpha boswellic acid, acetyl alpha boswellic acid, acetyl keto alpha boswellic acid, enoxolone, and pharmaceutically acceptable salts thereof. Carbenoxolone is also of interest. Other particularly preferred pentacyclic triterpenoid compounds include compound having a lupan core structure such as betulinic acid or a pharmaceutically acceptable salt thereof.

In accordance with the present invention, the at least one compound capable of reducing local subcutaneous fat is preferably administered as an injectable composition. The composition is not particularly limited any may be any pharmaceutically acceptable composition suitable for being injected into a subcutaneous fat layer (fat deposit) comprising the at least one fat reducing compound of the present invention. The term "pharmaceutically acceptable", as used herein, refers to materials or substances that are suitable for use in contact with the tissues of humans and mammals without undue toxicity, irritation, allergic response, and the like.

For example, the composition may be in the form of a solution, emulsion, suspension or dispersion, and may comprise said at least one compound capable of reducing local subcutaneous fat and a pharmaceutically acceptable carrier. The pharmaceutically acceptable carrier may be an aqueous solution (including water), an organic solvent, or a mixture of an aqueous solution and an organic solvent. Further, the injectable composition may be a buffered or non-buffered (in particular buffered), isotonic or hypertonic (in particular isotonic) aqueous or non-aqueous composition comprising the at least one fat reducing compound. Said pharmaceutically acceptable carrier serves as solvent for suspending the at least one fat reducing compound.

The at least one compound capable of reducing local subcutaneous fat may be present in the injectable composition in a concentration from about 0.001 wt. % to about 10 wt. %, preferably in a concentration of 0.01 to 5 wt. %, more preferably in an amount of 0.05 to 5% by weight, even more preferably in an amount of 0.07 to 3% or 0.1 to 2 wt. %, and most preferably in an amount of 0.1 to 1.5%, in particular 0.1 to 1.0% by weight.

Within the context of the present invention, the injectable composition of the at least one fat reducing compound may further comprise at least one additional pharmaceutically acceptable active ingredient. Said additional pharmaceutically acceptable ingredient, including ingredients promoting collagen biosynthesis, anti-inflammatory agents, polyols, vitamins, amino acids, metals, antioxidants, and mineral salts, are as defined hereinabove in relation to the injectable composition of hydroxyapatite particles. Further, the injectable composition of the at least one fat reducing compound may further comprise an anaesthetic agent. The anaesthetic is preferably a local anesthetic, preferably lidocaine, which is present in the injectable composition in a concentration of, for example, 0.05 wt. % to 5.0 wt. %, 0.1 wt. % to 4.0 wt. %, 0.2 wt. % to 3.0 wt. %, 0.3 wt. % to 2.0 wt. %, or 0.4 wt. % to 1.0 wt. %.

In a second aspect, the present invention relates to a method for treating gynoid lipodystrophy comprising administering to a subject in need thereof an effective amount of hydroxyapatite particles and an effective amount of at least one compound capable of reducing local subcutaneous fat, wherein the hydroxyapatite particles are administered concurrently, sequentially or separately with the at least one compound capable of reducing local subcutaneous fat.

With respect to the mode of administration, the description and definition of hydroxyapatite particles and the at least one compound capable of reducing local subcutaneous fat, the definition of terms, and other aspects, it is referred to the explanations, description and definitions given in relation to the first aspect of the present invention.

The hydroxyapatite particles as well as the at least one compound capable of reducing local subcutaneous fat is usually locally injected using a syringe and an injection needle having a suitable diameter and length. For example, a syringe with a 30G injection needle may be used for injection of hydroxyapatite particles, and a syringe with a 33G needle may be used for injection of the at least one fat reducing compound. The injection needles may suitably have a length of between half an inch and one and a half inch.

Furthermore, it is also contemplated that injection of the hydroxyapatite particles and/or the at least one fat reducing compound is carried out using needles that are filled with the substance or composition to be administered and are bioresorbable. After implantation of the bioresorbable needles into the skin, each needle is separated from its carrier by contact with the body fluids. It is further contemplated that injection of the hydroxyapatite particles and/or the at least one fat reducing compound is carried out by means of a micro-needle system, wherein the micro-needle system comprises a flexible base layer into which micro-needles of different lengths are integrated such that the tips of the micro-needles perpendicularly project from the plane of the base layer.

Suitably, the micro-needles of said micro-needle system have two different lengths, wherein the shorter micro-needles are filled with or are intended to be filled with an injectable composition comprising hydroxyapatite particles, and wherein the longer micro-needles are filled with or are intended to be filled with an injectable composition comprising the at least one fat reducing compound, such that the composition containing hydroxyapatite particles is delivered into the dermis, especially the deep dermis, wherein the composition containing the at least one fat reducing compound is delivered into the subcutis, more specifically into the subdermal fat layer.

The tip of at least one of the micro needles, preferably the tip of each micro needle of the micro-needle device may be made of a bio-resorbable material such as, for example, poly-lactide (PLA) or poly-hydroxybutyrate (PHB). Further, the micro-needle device may be configured such that the bio-resorbable micro-needles can be separated from the base layer upon contact with the body fluids. The tip of the needle itself may be formed of hydroxyapatite with a biodegradable bridge made from, e.g. PLA. Using this configuration, the needle tip itself will be released in the tissue after application of the micro-needle patch. Those skilled in the art will be readily able to select an appropriate syringe and injection needle depending on the substance or composition to be injected, the site of injection, the amount or volume to be applied, etc.

In a third aspect, the present invention provides a kit comprising a composition containing hydroxyapatite particles and a composition containing at least one compound capable of reducing local subcutaneous fat, and optionally instructions for use.

Preferably, the composition containing hydroxyapatite particles and/or the composition containing the at least one fat reducing compound are present in the kit in form of injectable compositions. This provides a kit that is ready to use in treating gynoid lipodystrophy.

In another variation of the kit, the composition containing hydroxyapatite particles and/or the composition containing the at least one fat reducing compound are not present in a form ready for being injectable, i.e. in liquid form, but as a powder, in form of granules or as a tablet. For use, the powder, granules or tablets has to be dissolved or suspended in a solvent before being administrable by injection.

The kit may also comprise at least one vial containing a solvent for dissolving or suspending the composition containing hydroxyapatite particles and/or the composition containing the at least one fat reducing compound. This provides the advantage that the amount and/or concentration of the hydroxyapatite particles and/or the at least one fat reducing compound can be adjusted to the patient's needs prior to its administration.

Furthermore, the kit may comprise means for administering the composition(s). For example, said means for administering one or both of the compositions may be at least two syringes, each provided with or to be provided with an injection needle of specific length for targeting the desired tissue. It is also within the scope of the present invention that said means are configured as a specific application device, which allows for the simultaneous delivery of the two different compositions in different depths of the skin of a patient.

In a specific embodiment, the means are configured such that the amount to be delivered to the patient is individually adjustable for each composition. In particular, the kit may comprise the micro-needle system described above in connection with the second aspect of the present invention. The syringe(s) and the micro-needle systems may be present in the kit as such, i.e. empty, or may be pre-filled with an injectable composition of hydroxyapatite particles and/or an injectable composition of the at least one fat reducing compound.

Where an indefinite or definite article is used when referring to a singular noun, e.g. "a", "an", "the", this includes a plural of that noun unless something else is specifically stated. It is to be noticed that the term "comprising", used in the present description and claims, should not be interpreted as being restricted to the means listed thereafter; it does not exclude other elements or steps. Thus, the scope of the expression "a composition comprising components A and B" should not be limited to compositions consisting only of components A and B. It means that also other components may be included in the composition.

EXAMPLES

The following examples are provided for ease of understanding of the present invention and are included only for illustrative purposes without imposing any limitations upon the claimed invention.

Example 1

Ex Vivo Preliminary Tests

The ex vivo preliminary tests described in this example were carried out to establish suitable parameters for clinical development and involved co-injection of hydroxyapatite particles and polidocanol into the thigh of a dead female mammalian body, followed by assessing their tissue distribution.

Specifically, small deposits of hydroxyapatite particles were provided in the lower dermis/upper subcutis by injecting a composition comprising 55.7 wt. % calcium hydroxyapatite particles (mean diameter of 25-45 µm), 36.6 wt. % sterile water for injection (USP), 6.4 wt. % glycerin (USP) and 1.3 wt. % sodium carboxymethyl cellulose (USP), supplemented with a red dye for improved visualization.

The composition was injected in a volume of 0.03 ml to 0.05 ml per injection point into the thigh at a depth of 5 mm, 8 mm or 10 mm and at an angle of about 60° using a 25G, 27G or 30G injection needle. Injections were spaced apart from each other by about 0.5 cm, 1.0 cm or 2.0 cm. Likewise small amounts (0.05 ml or 0.1 ml) of 0.5% or 2% polidocanol in aqueous methylene blue were injected into the upper subcutaneous tissue of the other thigh, the injections being spaced apart from each other by about 0.5 cm, 1.0 cm, 1.5 cm, 2.0 cm or 3.0 cm.

About 30 minutes after injection, macrosections were prepared and the distribution of the red or blue dye within the tissue was determined. It was found that the red dye of the hydroxyapatite composition is present within the superficial fat lobules of the subcutis. The blue dye representing polidocanol, on the other hand, was hardly present in the fat lobules, but was observed to accumulate in the septa between the fat lobules. The preparation was also found to be very evenly distributed in the dermis.

In view of these results, it was concluded that (1) the needle used for injecting polidocanol into the upper subcutis should have a length of about 8-10 mm, (2) the preparation comprising 2% polidocanol shows better distribution characteristics than the preparation comprising 0.5% polidocanol, and (3) the distance between individual injections is most suitably about 1 cm since this distance was found to result in a confluent and even distribution throughout the tissue.

Furthermore, regarding the injection of hydroxyapatite particles, it was concluded that (1) the injection should preferably occur in a depth of at most 5 mm for reaching the lower dermis, (2) a distance of about 1 cm between individual injections is most suitable for obtaining an even distribution throughout the tissue.

Example 2

Patient Study

Materials and Methods
Patients

Three healthy skin patients aged 23, 27, and 39 years with moderately severe cellulite on thighs (total score of 6 to 10 on the Cellulite Severity Scale (CSS) according to Hexsel et al., (the "Hexsel, Dal'Forno, and Hexsel Cellulite Severity Scale"; see Hexsel et al., A validated photonumeric cellulite severity scale, J. Eur. Acad. Dermatol. Venereol. 2009, 23: 523-528), a body mass index (BMI) below 30, and a waist-hip ratio of s 0.6 were included in the patient study. However, two of the three patients were prematurely withdrawn from the study due to pregnancy ("drop-outs"), and were thus not evaluated.
Products Radiesse® (Merz, Frankfurt a. M., Germany) is a soft tissue filler which comprises calciumhydroxyapatite (Ca-HAP) particles dispersed in a carrier gel of carboxymethyl cellulose (CMC) that further includes glycerol.

Aethoxysklerol® 0.5% is an injection solution which contains polidocanol as active agent in a concentration of 0.5% w/v (10 mg in 2 ml of injection solution).
Therapy Regimen At day 0 and day 21±10 days, 2 ml of a diluted Aethoxysklerol® solution (Aethoxysklerol® 0.5% diluted 1:1 with 2% aqueous lidocaine) were subcutaneously injected in each thigh. At day 42, calcium hydroxyapatite particles were administered by deep intradermal injection of 3 ml diluted Radiesse® (Radiesse® diluted 1:1 with 2% aqueous lidocaine) in each thigh.

The injections were performed by serial, selective injection on the first, second and third appointment. Before the injections, a tattoo mask was applied to the areas of the thighs to be treated for the standardization of injection points (150 points with spacing of 1 cm). The injection depth was sonographically controlled. A 33G needle and a 30G needle were used for Aethoxysklerol® and calcium hydroxyapatite (Radiesse®), respectively. The volume per injection point was 0.1 ml for Aethoxysklerol® and between 0.015 ml to 0.02 ml for Radiesse®. The treatment was found to be well tolerated without any notable side-effects.

Data were collected at day 0, day 84, and day 168 at the Department of Cosmetics Science at the University of Hamburg using the test methods described below. As mentioned above, the two-drop-outs" reduced the number of patients evaluated from three to one.
Test Methods
Cutometry:

The elasticity of skin was measured using a commercial cutometer. The measuring principle is based on the so-called suction method. A negative pressure is produced in the measuring head, and the skin is drawn inside the instrument, and after a defined time released again. An optical measuring system measures the light intensity, which varies in accordance with the degree of skin penetration. The resistance of the skin to the negative pressure (firmness) and its ability to return into its original position (elasticity) are displayed as curves (penetration depth in mm/time) in real time during the measurement.

The parameters determined from the measurement curves included, inter alia, the R2 (gross elasticity), R5 (the net elasticity), and R6 (viscoelasticity) parameters. R2 is a measure of the gross elasticity of the skin (resistance versus ability of returning). The closer R2 is to 100%, the more elastic the skin. Likewise, the closer the value of R5 (net elasticity, i.e. the elastic portion of the suction part versus the elastic portion of the relaxation part) is to 100%, the more elastic the skin. The parameter R6 (viscoelasticity) indicates the portion of the viscoelasticity of the curve. The smaller this value is, the higher the elasticity of skin.
Sonography:

The thickness of the dermis (often referred to as "skin thickness") and the skin density were assessed by 20 MHz ultrasound examination using a DUB® ultrasound scanner (tpm, Lüneburg, Germany).
Cellulitis Severity Rating:

The severity of cellulite was rated using the total score from the Hexsel, Dal'Forno, and Hexsel Cellulite Severity Scale (CSS) (Hexsel et al. (2009), supra). The Hexsel et al. rating score consists of the following criterions: (a) number of evident depressions, (b) depth of depressions, (c) morphological appearance of skin surface alterations, (d) grade of laxity, flaccidity or sagging skin, (e) classification scale by the Nürnberger-Müller scale. The rating was carried out by the patients themselves and by a blinded expert. Each item was graded from 0 to 3, allowing final classification of cellulite as mild (1-5 points), moderate (6-10 points), and severe (11-15 points).
Patient Questionnaire on Quality of Life:

The quality of life (QoL or QoI) was assessed using a patient questionnaire (CelluQoI@) (Hexsel D, Weber M, Tabord M L, Fonte de Souza J., Preliminary results of the elaboration of a new instrument to evaluate quality of life in patients with cellulite-CelluQoI®, Poster AAD 2012). Each question was rated from 1 to 5 as follows: 1=not bothered at all, 2=not bothered most of the time, 3=no feelings either way, 4=bothered most of the time, 5=bothered all the time
Results The results obtained are summarized in Table 1 below. As can be seen, the gross elasticity and the net elasticity at day 168 were slightly increased and slightly decreased, respectively. The viscoleasticity (R6) decreased (day 0: R6=51%, day 84: R6=26%, and day 168: R6=35%). It is noted that the significantly decreased elasticity parameters on day 84 can be explained by seasonal variations (summer for first measurements, and winter for second and third measurements).

The skin thickness significantly increased from day 0 to day 168 (1262 µm to 1680 µm), and the skin density decreased from day 0 (26) to day 84 (25) to day 18 (21). Further, the mean weight of the patient decreased from 59 kg at the beginning to 55 kg after 168 days, and the thigh circumference also significantly decreased from 57.8 cm to 55.5 cm.

Furthermore, a slight improvement in the severity of cellulite was observed by both the patient and the expert. At day 0, the cellulite was assessed as being "moderate" (score of 7), after 84 days the cellulite improved to a "mild" state (score of 3.5), and after 168 days the cellulite severity was improved by 1 point (score of 6) compared to the initial value at day 0.

Moreover, the body-related quality of life improved in all factors assessed except for "clothing manners": skin appearance (from 3 to 2 after 168 days), clothing manners (from 3 to 3 after 168 days), feeding habits (from 3 to 2 after 168 days), physical and leisure activities involving exposure of the body in public (from 4 to 3 after 168 days), physical or recreational activities involving the restricted exposure of the body (from 4 to 1 after 168 days), sexual life (from 4 to 2 after 168 days), and self-confidence (from 3 to 2 after 168 days).

TABLE 1

Results of treatment with Aethoxysklerol ® 0.5% and calcium hydroxyapatite particles (Radiesse ®)

| PARAMETER | DAY 0 | DAY 84 | DAY 168 |
|---|---|---|---|
| Skin elasticity | | | |
| gross elasticity (R2) [%] | 83 | 72 | 88 |
| net elasticity (R5) [%] | 89 | 60 | 83 |
| viscoelasticity (R6) [%] | 51 | 26 | 35 |
| Skin thickness and density | | | |
| thickness [µm] | 1262 | 1477 | 1680 |
| density | 26 | 25 | 21 |
| Severity of cellulite | | | |
| expert | 7 | 3 | 6 |
| patient | 7 | 4 | 6 |
| Body figures | | | |
| weight [kg] | 59.0 | 57.2 | 55.0 |
| circumference of thighs [cm] | 57.8 | 55.5 | 55.5 |
| CelluQol ® questionnaire | | | |
| skin appearance | 3 | 2 | 2 |
| clothing manners | 3 | 3 | 3 |
| feeding habits | 3 | 3 | 2 |
| physical and leisure activities involving exposure of the body in public | 4 | 4 | 3 |
| physical or recreational activities involving the restricted exposure of the body | 4 | 1 | 1 |
| sexual life | 4 | 3 | 2 |
| self-confidence | 3 | 2 | 2 |

The results show that the combined use of Aethoxysklerol® 0.5% and Radiesse® leads to a significant improvement of skin elasticity and skin firmness, as evidenced by the positive change of the cutometry parameters, as well as to a stabilization of the dermis, as evidenced by the results of high-frequency ultrasound measurements.

Furthermore, the reduced body weight and circumference of thighs resulted in a significantly slimmer silhouette, in line with the positive evaluation in this respect by the patient. Also, the quality of life was clearly improved. Overall, the patients expectation was met and the patient was satisfied with the treatment outcome.

Thus, the results show that the treatment with calcium hydroxyapatite particles (Radiesse®) in combination with polidocanol (Aethoxysklerol® 0.5%) is efficient in the treatment of cellulite (gynoid lipodystrophy), and thus offers a new promising treatment option.

The invention claimed is:

1. A method for treating gynoid lipodystrophy comprising administering to a subject in need thereof an effective amount of calcium (hydroxy)phosphate particles in an injectable hydrogel composition and an effective amount of at least one compound capable of reducing local subcutaneous fat in an injectable composition,
   wherein the compound capable of reducing local subcutaneous fat is polidocanol,
   wherein the treatment comprises local injection of the injectable composition of polidocanol into the subcutis, and sequential local injection of the injectable hydrogel composition of calcium (hydroxy)phosphate particles into the dermis,
   wherein the injectable hydrogel composition comprises the calcium (hydroxy)phosphate particles and at least one polysaccharide, the polysaccharide(s) being cross-linked and/or non-crosslinked, and the calcium (hydroxy)phosphate particles are present in the composition in an amount of about 5 to 45 vol. % and the polysaccharide(s) are present in the composition in an amount of about 0.01-5.0%,
   wherein the injectable composition comprises polidocanol in an amount from about 0.05 wt. % to about 5 wt. %, based on the total weight of the injectable composition,
   wherein the calcium (hydroxy)phosphate particles and the at least one compound capable of reducing local subcutaneous fat are the only active ingredients, and
   wherein the calcium (hydroxy)phosphate particles and/or the at least one compound capable of reducing local subcutaneous fat are administered more than once, and the interval between any two consecutive administrations of the calcium (hydroxy)phosphate particles and/or the at least one compound capable of reducing local subcutaneous fat is about 1 week to about 8 weeks.

2. The method of claim 1, wherein the calcium (hydroxy)phosphate particles are selected from the group consisting of monocalcium phosphate (MCP), dicalcium phosphate (DCP), calcium dihydrogen phosphate (CDP), tricalcium phosphate (TCP) including its α-, α'- and β-polymorphs, octacalcium phosphate (OCP), biphasic tricalcium phosphate (BCP), and hydroxyapatite.

3. The method of claim 1, wherein the calcium (hydroxy)phosphate particles and the at least one compound capable of reducing local subcutaneous fat are administered to a subject having a body mass index (BMI), defined as the body mass in kg divided by the square of the body height, of at least 25 kg/m$^2$, or to a subject having severe cellulite corresponding to a total sum of scores of items (a) and (b)

of the Hexsel, Dal'Forno, and Hexsel Cellulite Severity Scale (CSS) of 4, 5 or 6, wherein item (a) denotes the number of evident depressions and item (b) denotes the depth of depressions, and both item (a) and item (b) are graded from 0 to 3.

4. The method of claim 1, wherein the calcium (hydroxy) phosphate particles have a mean size of about 20 μm to about 70 μm in diameter, or a D-ratio of equal to or greater than 0.9, or both, wherein the D-ratio is defined as the ratio of the calculated diameter of a perfect circle based on the cross sectional area of the particle to the maximum diameter measured through that cross sectional centroid.

5. The method of claim 1, wherein the injectable composition further comprises one or more polyols in a total amount of 0 vol. % to 20 vol. %, or at least one additional pharmaceutically acceptable ingredient, in an amount of 0.001 to 5 vol. %, or both.

6. The method according to claim 1, wherein the at least one compound capable of reducing local subcutaneous fat is selected from the group consisting of
  (i) compounds that stimulate the β2-adrenergic pathway directly or block the activity of cellular phosphodiesterases,
  (ii) adipocytolytic compounds,
  (iii) proapoptotic compounds,
  (iv) compounds impairing differentiation of pre-adipocytes,
  (v) pentacyclic triterpenoid compounds,
  (vi) other compound comprising fluoxetine, glycyrrhizic acid, maslinic acid, ginsenoide Rh2, betulinic acid, moronic acid, deoxycholic acid, obeticholic acid, erythrodoil, ursolic acid, uvaol, betulinic acid, becarben, carbenoxolone, or glabridin, and
  (vii) combinations of one or more of (i) to (vi).

7. The method of claim 1, wherein the at least one compound capable of reducing local subcutaneous fat is administered as an injectable composition, in the form of a solution, emulsion, suspension or dispersion, comprising said at least one compound capable of reducing local subcutaneous fat and a cosmetically acceptable carrier selected from the group consisting of an aqueous solution, an organic solvent, or a mixture of an aqueous solution and an organic solvent.

8. The method of claim 1, wherein the polysaccharide(s) is carboxymethyl cellulose (CMC), hyaluronic acid (HA), or a mixture thereof.

9. The method of claim 5, wherein the one or more polyols is glycerol, and the at least one additional pharmaceutically acceptable ingredient is a local anesthetic.

10. The method of claim 1, comprising administering to the subject in need thereof a combination consisting essentially of the effective amount of calcium (hydroxy)phosphate particles and the effective amount of at least one compound capable of reducing local subcutaneous fat.

11. The method of claim 1, comprising administering to a subject in need thereof a combination consisting of the effective amount of calcium (hydroxy)phosphate particles, the effective amount of at least one compound capable of reducing local subcutaneous fat, at least one polysaccharide, glycerol, buffer, water, and ethanol.

12. The method of claim 1, comprising administering to a subject in need thereof a combination consisting of the effective amount of calcium (hydroxy)phosphate particles, the effective amount of at least one compound capable of reducing local subcutaneous fat, at least one polysaccharide, glycerol, buffer, water, ethanol, and at least one further ingredient selected from the group consisting of an ingredient which promotes collagen biosynthesis, an anesthetic, an anti-inflammatory agent, a polyol, a vitamin, an amino acid, a metal, an antioxidant, and a mineral salt.

13. The method of claim 1, wherein the polysaccharide(s) is a mixture of carboxymethyl cellulose (CMC) and hyaluronic acid (HA).

14. The method of claim 1, wherein the polysaccharide(s) is present in an amount of about 0.1% to 4.0%.

15. The method of claim 1, wherein the polysaccharide(s) is present in an amount of about 1.0% to 2.5%.

16. The method of claim 1, wherein the injectable composition comprises polidocanol in an amount from about 0.1 wt. % to about 1 wt. %, based on the total weight of the injectable composition.

17. The method of claim 1, wherein the treatment reduces the volume of local subcutaneous fat by at 25% to 70%.

* * * * *

UNITED STATES PATENT AND TRADEMARK OFFICE
CERTIFICATE OF CORRECTION

| | |
|---|---|
| PATENT NO. | : 11,344,573 B2 |
| APPLICATION NO. | : 16/344086 |
| DATED | : May 31, 2022 |
| INVENTOR(S) | : Harry Frank Abts et al. |

It is certified that error appears in the above-identified patent and that said Letters Patent is hereby corrected as shown below:

On the Title Page

Item (12) delete "Abst" and insert --Abts--.

In item (72) "Inventors," please delete "Harry Frank Abst, Oberursel (DE)" and insert --Harry Frank Abts, Oberursel (DE)--.

Signed and Sealed this
Eighth Day of November, 2022

Katherine Kelly Vidal
*Director of the United States Patent and Trademark Office*